United States Patent
Muller

(10) Patent No.: US 9,107,633 B2
(45) Date of Patent: Aug. 18, 2015

(54) MEDICAL WORK STATION

(75) Inventor: Michael Muller, Augsburg (DE)

(73) Assignee: KUKA Roboter GmbH, Augsburg (DE)

( * ) Notice: Subject to any disclaimer, the term of this patent is extended or adjusted under 35 U.S.C. 154(b) by 453 days.

(21) Appl. No.: 13/097,391

(22) Filed: Apr. 29, 2011

(65) Prior Publication Data

US 2012/0029694 A1  Feb. 2, 2012

(30) Foreign Application Priority Data

Aug. 2, 2010 (DE) .......................... 10 2010 038 800

(51) Int. Cl.
*G05B 19/418* (2006.01)
*A61B 6/00* (2006.01)
*A61B 6/04* (2006.01)
*A61B 19/00* (2006.01)

(52) U.S. Cl.
CPC .............. *A61B 6/4458* (2013.01); *A61B 6/0407* (2013.01); *A61B 6/0457* (2013.01); *A61B 6/4441* (2013.01); *A61B 6/4452* (2013.01); *A61B 19/2203* (2013.01); *A61B 6/4464* (2013.01); *A61B 2019/2223* (2013.01); *A61B 2019/5238* (2013.01)

(58) Field of Classification Search
CPC .. A61B 6/4458; A61B 6/0407; A61B 6/0457; A61B 6/4441; A61B 6/4452; A61B 6/4464; A61B 19/2203; A61B 2019/2223; A61B 2019/5238
USPC .......................................................... 700/248
See application file for complete search history.

(56) References Cited

U.S. PATENT DOCUMENTS

| | | | | |
|---|---|---|---|---|
| 4,894,855 | A * | 1/1990 | Kresse | 378/196 |
| 6,200,024 | B1 * | 3/2001 | Negrelli | 378/197 |
| 2008/0119714 | A1 | 5/2008 | Meissner et al. | |
| 2009/0024025 | A1 | 1/2009 | Maschke et al. | |
| 2011/0026669 | A1 * | 2/2011 | Tancredi et al. | 378/19 |

(Continued)

FOREIGN PATENT DOCUMENTS

| DE | 10 2008 016 414 A1 | 10/2009 |
|---|---|---|
| DE | 10 2008 019 345 A1 | 10/2009 |

(Continued)

OTHER PUBLICATIONS

European Patent Office; Search Report in European Patent Application No. 11174482 dated Nov. 23, 2011; 6 pages.

(Continued)

*Primary Examiner* — Khoi Tran
*Assistant Examiner* — Adam Mott
(74) *Attorney, Agent, or Firm* — Wood, Herron & Evans, LLP

(57) ABSTRACT

The invention relates to a medical work station which has a medical technology apparatus and a patient support device. The medical technology apparatus includes a medical technology device and at least one first robot, which has a first robot arm, having a plurality of members and a first control device that controls a motion of the first robot arm. The medical technology device is attached to a first attaching device of the first robot arm. The patient support device includes a patient table and a second robot, which has a second robot arm having a plurality of members, and a second control device that controls a motion of the second robot arm. The patient table is attached to a second attaching device of the second robot arm.

8 Claims, 2 Drawing Sheets

(56) References Cited

U.S. PATENT DOCUMENTS

2011/0054688 A1* 3/2011 Ortmaier et al. ............. 700/255
2011/0069818 A1* 3/2011 Muller ......................... 378/197

FOREIGN PATENT DOCUMENTS

| DE | 102008016414 A1 * | 10/2009 |
| DE | 10 2008 022 924 A1 | 11/2009 |
| WO | 2006/069288 A2 | 6/2006 |

OTHER PUBLICATIONS

German Patent Office; Office Communication in German Patent Application No. 10 2010 038 800.9 dated Feb. 23, 2011; 4 pages.

* cited by examiner

MEDICAL WORK STATION

TECHNICAL FIELD

The invention relates to a medical work station which includes a medical technology apparatus and an adjustable patient-supporting device. The medical technology apparatus and the patient-supporting device each include at least one robot.

BACKGROUND

Robots are working machines, which are equipped with tools for automatic handling and/or processing of objects, and are programmable in a plurality of motion axes, for example with regard to orientation, position and process sequence. Robots usually have a robot arm with a plurality of members connected via joints, and programmable controllers (control devices) which control or regulate the motion sequences of the robot during operation. The members are moved by means of drives which are activated by the control device, in particular in reference to the axes of motion.

DE 10 2008 019 345 A1 discloses a medical work station having an x-ray apparatus and a patient table. The x-ray apparatus has a robot, to whose robot arm a C-shaped arc with an x-ray source and an x-ray receiver are attached. The patient table is attached to a robot arm of another robot.

DE 10 2008 016 414 A1 discloses a medical work station having a patient table and an x-ray device. The x-ray source of the x-ray device is attached to a robot arm of a robot, and the x-ray receiver is attached to a robot arm of another robot. The control devices of the two robots are coupled with each other and designed as a master-slave system, wherein one of the control devices is designed as the master and the other control device is designed as the slave. The control device designed as the master activates the control device designed as a slave in such a way that the x-ray source and the x-ray receiver are always oriented to each other at a predefined distance.

The object of the invention is to specify an improved medical work station having a medical technology apparatus and a patient support device, wherein the medical technology apparatus and the patient support device each have at least one robot.

SUMMARY

The object of the invention is fulfilled by a medical work station having
  a medical technology apparatus which has a medical technology device and at least one first robot, which has a first robot arm having a plurality of members and a first control device controlling a motion of the first robot arm, the medical technology device being attached to a first attaching device of the first robot arm, and
  a patient support device that has a patient table and a second robot, which has a second robot arm having a plurality of members and a second control device controlling a motion of the second robot arm, the patient table being attached to a second attaching device of the second robot arm,
the two control devices being coupled with each other and designed as a master-slave system, wherein one of the control devices is designed as the master and the other control device is designed as the slave, the control device designed as the master activates the control device designed as a slave in such a way that at a first motion of the attaching device of the robot whose control device is designed as the master, the control device designed as the slave moves its robot arm in such a way that the attaching device of the robot whose control device is designed as the slave executes a second motion, on the basis of which the patient table and the medical technology device are always oriented relative to each other in a defined way, in particular remaining constant.

Accordingly, the medical work station according to the invention has at least two robots, each of which includes a plurality of axes, and each of which has an attaching device, in particular a flange. One of the robots is part of the patient support device, on whose patient table a living organism may lie, for example during a treatment with the medical technology apparatus. The other robot or robots are part of the medical technology apparatus.

The medical technology device is designed for example as an imaging medical technology device. One example of an imaging medical technology device is an x-ray device.

Each of the robots includes its own control device. The respective control devices control their respective robot arms during operation of the medical work station according to the invention. To that end, as is generally known to a person skilled in the art, the robots may be provided with electric drives, which are activated in turn by the relevant control devices. Hence the medical work station according to the invention does not include a central control device that activates all of the axes of the robots together. As a result, it is possible to use two or more standard robots, each having a control apparatus intended for it. This can result in a more flexible embodiment of the medical work station according to the invention.

According to the invention, in at least one operating mode of the medical work station the orientation of the patient table should always be defined relative to it, in particular remaining constant. In order to achieve this, the control devices are coupled together and are designed as a master-slave system. One of the control devices is designed in this case as the master and the second control device is designed as the slave.

The medical work station according to the invention can be set up so that the patient table is always centered in reference to the x-ray receiver and x-ray source, i.e., so that the patient table is always at the same distance from the x-ray receiver and the x-ray source. It is also possible, however, that the distance between the patient table and the x-ray receiver and the distance between the patient table and the x-ray transmitter differ, but in particular always remain constant. The two distances may be, for example, at a ratio of 1:2, 2:3, 1:4.

During operation of the medical work station it is accordingly possible that the control device designed as the master, during the first motion of the attaching device of its robot, activates the control device designed as the slave, so that the latter in turn activates its robot arm in such a way that the relevant attaching device follows the first motion of the other attaching device in such a way that orientations of the medical technology device and the patient table are always defined relative to each other, in particular remaining constant.

In this case it may be provided that either the first or the second control device is designed as the master. If the first control device, for example, is designed as the master, then the patient table automatically follows a motion of the medical technology device. If the second control device is designed as the master, the medical technology device automatically follows a motion of the patient table.

According to one embodiment of the medical work station according to the invention, the control device designed as the master automatically activates its robot arm in such a way that the relevant attaching device executes the first motion.

According to this variant, the result is a fully automatic motion of the entire medical work station.

It is also possible that the first motion is executed manually. This occurs, according to one embodiment of the medical work station according to the invention, through manual guiding of at least one part of the medical technology device, or on the basis of manual guiding of the patient table or of the relevant robot arm.

According to another embodiment of the medical work station according to the invention, the latter, coupled with the control device designed as the master, has input means with which the control device designed as the master activates its robot arm in such a way that the relevant attaching device executes the first motion on the basis of a manual input into the input means. The manual input means are for example a manual operating apparatus.

According to another embodiment of the medical work station, during the first motion the control device designed as the master conveys to the control device designed as the slave information about the current position and orientation of its attaching device. On the basis of the relative position of the robot arm whose control device is designed as the master, relative to the robot arm whose control device is designed as the slave, and on the basis of the information about the current position and orientation of the attaching device of the robot whose control device is designed as the master, the control device designed as the slave can then move the robot arm of the robot whose control device is designed in the slave in such a way that the attaching device of this robot has a position and orientation in which the orientations of the patient table and the medical technology device are always defined relative to each other, in particular remaining the same.

If the control device of the robot that is part of the medical apparatus is designed as the master, then it may also be provided that this control device conveys information about the current position and orientation of the medical technology device situated on its attaching device.

If the control device of the robot that is part of the patient support device is designed as the master, then it may also be provided that this control device conveys information about the current position and orientation of the patient table situated on its attaching device.

Depending on the embodiment, the medical work station according to the invention allows an adjustment to be realized between the positions of the patient positioner or patient supporting device and at least one other medical technology apparatus without additional external control. As a result, a time delay may be at least partially, if not indeed largely eliminated, and the fluctuations in the distance between the patient positioner or patient support device and the medical technology apparatus at least reduced, if not indeed minimized or prevented. The effort for a collision calculation can be relatively small.

For the medical work station according to the invention, depending on the embodiment, a robot-based patient positioner or robot-based patient support device is employed, and in addition at least one medical technology apparatus is guided per robot. The two robot-based systems may in particular be positioned synchronously with each other. A relative orientation is also possible, which is always clearly definable.

By employing a collision-avoidance system, it is also possible to prevent collisions between the patient positioner or patient support device and the medical technology apparatus.

BRIEF DESCRIPTION OF THE DRAWINGS

Examples of exemplary embodiments of the invention are depicted in the accompanying schematic drawing. The figures show the following.

DETAILED DESCRIPTION

Figure 1:
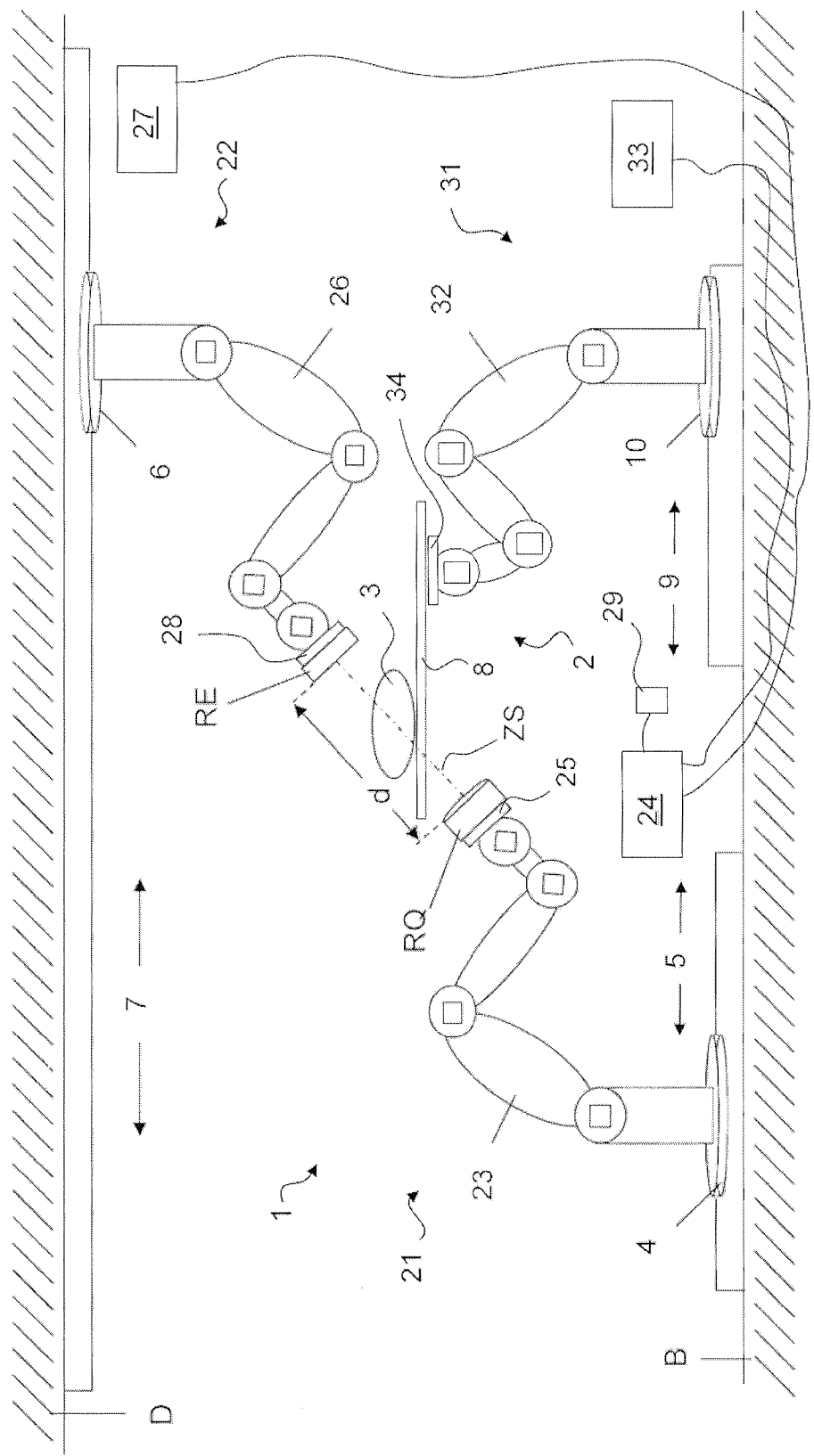
FIG. 1 a medical work station, and
FIG. 2 another medical work station.

FIG. 1 shows a medical work station having an x-ray device 1 and an adjustable patient support device 2 for supporting a living organism 3. X-ray device 1 is an example of a medical technology apparatus, and in particular an example of an imaging medical technology apparatus.

The x-ray device 1 shown in FIG. 1 has a first robot 21 and a second robot 22, as well as an x-ray source RQ and an x-ray receiver RE.

First robot 21 has a robot arm 23 and a control device 24. Robot arm 23 includes a plurality of members, joints connecting the members, drives connected to the control device 24 in a manner not shown, in particular electric drives for moving the members, and an attaching device 25 for example in the form of a flange. A computer program runs on control device 24, so that control device 24 activates the drives in such a way that the position and orientation of attaching device 25 may be oriented essentially freely in space. The electric drives of first robot 21 each include for example an electric motor and possibly power electronics that activate the motors. Attached to attaching device 25 of robot arm 23 of first robot 21 is x-ray source RQ.

Second robot 22 has a robot arm 26 and a control device 27. Robot arm 26 includes a plurality of members, joints connecting the members, drives connected to the control device 27 in a manner not shown, in particular electric drives for moving the members, and an attaching device 28 for example in the form of a flange. A computer program runs on control device 27, so that control device 27 activates the drives in such a way that the position and orientation of attaching device 28 may be oriented essentially freely in space. The electric drives of second robot 22 each include, for example, an electric motor and possibly power electronics that activate the motors. Attached to attaching device 28 of robot arm 26 of second robot 22 is x-ray receiver RE.

In the case of the present exemplary embodiment, patient support device 2 includes a patient table 8 and a third robot 31. Living organism 3 lies on patient table 8.

Third robot 31 has a robot arm 32 and a control device 33. Robot arm 32 includes a plurality of members, joints connecting the members, drives connected to the control device 33 in a manner not shown, in particular electric drives for moving the members, and an attaching device 34 for example in the form of a flange. A computer program runs on control device 33, so that control device 33 activates the drives in such a way that the position and orientation of attaching device 34 may be oriented essentially freely in space. The electric drives of third robot 31 each include for example an electric motor and possibly power electronics that activate the motors. Attached to attaching device 34 of robot arm 32 of third robot 31 is patient table 8.

In the case of the present exemplary embodiment, first robot 21 or its robot arm 23 is attached to a linear unit 4, which is attached to the floor B of the medical work station and in particular is rail-bound, by means of which first robot 21 or its robot arm 23 is movable along a double arrow 5. Second robot 22 or its robot arm 26 is attached to a linear unit 6, which is attached to the ceiling D of the medical work station and in particular is rail-bound, by means of which second robot 22 or its robot arm 26 is movable along a double arrow 7. Third robot 31 or its robot arm 32 is attached to a linear unit 10, which is attached to the floor B of the medical work station and in particular is rail-bound, by means of which third robot 31 or its robot arm 32 is movable along a double arrow 9.

Linear units 4, 6, 10 each include drives which are not depicted in the figures, the drive of the linear unit 4 assigned to first robot 21 being connected to control device 24 of first robot 21, the drive of the linear unit 6 assigned to second robot 22 being connected to control device 27 of second robot 22, and the drive of the linear unit 10 assigned to third robot 31 being connected to control device 33 of third robot 31.

During operation of robots 21, 22, 31, control device 24 of first robot 21 controls the linear unit 4 assigned to first robot 21, in order to move robot arm 23 of first robot 21 along double arrow 5, control device 27 of second robot 22 controls the linear unit 6 assigned to second robot 22, in order to move robot arm 26 of second robot 22 along double arrow 7, and control device 33 of third robot 31 controls the linear unit 10 assigned to third robot 31, in order to move robot arm 32 of third robot 31 along double arrow 9.

In the case of the present exemplary embodiment, in a first operating mode, for example, a physician, not depicted in further detail in the figures, is able to operate first robot 21, by means of a user interface 29 connected to the robot's control device 24, in such a way that control device 24 activates the drives of first robot 21 so that attaching device 25 of robot arm 23 of first robot 21, and thus x-ray source RQ, executes a motion determined by the physician. Thus it is possible for the physician to orient the x-ray source RQ relative to living organism 3 in a desired manner, in order to produce an x-ray image of a region of the body of living organism 3.

For the x-ray image that the physician is able, for example, to trigger by means of an input means of user interface 29, not depicted in further detail, x-ray source RQ generates x-ray radiation having a central beam ZS.

For the recorded image, the x-ray radiation is partially attenuated as it passes through living organism 3, and strikes x-ray receiver RE. The latter converts the incident x-ray radiation into an electrical signal corresponding to the x-ray radiation, to which signal is assigned in turn an x-ray image, not depicted in further detail, of the relevant body region of living organism 3. The x-ray image may be viewed, for example, by means of a display screen, not depicted in further detail for the sake of clarity.

So that the x-ray image will be of at least satisfactory quality, during the recording of the x-ray image the x-ray receiver RE should be oriented relative to x-ray source RQ at a predefined distance d. In the case of the present exemplary embodiment, it may also be provided that patient table 8 is always oriented relative to x-ray source RQ or to x-ray receiver RE in a defined manner, in particular remaining constant. This is realized as follows in the case of the present exemplary embodiment:

The control devices 24, 27, 33 of the three robots 21, 22, 31 are designed as a master-slave system, control device 24 of first robot 21 being designed in the case of the present exemplary embodiment as the master, and control devices 27, 33 of second robot 22 and of third robot 31 being designed as slaves. Based on the input into user interface 29, control device 24 activates the electric drives of first robot 21 and possibly of linear unit 4 in such a way that attaching device 26 of first robot 21 and thus x-ray source RQ execute the motion.

At the same time, control device 24 of first robot 21 conveys to control device 27 of second robot 22 and to control device 33 of third robot 31 information about the current position and orientation of its attaching device 25, which in the case of the present exemplary embodiment represents information about the position and orientation of a coordinate system assigned to this attaching device 25. Control devices 27, 33 of second and third robots 22, 31 also have access to information about the relative location (orientation and position) between the coordinate system of attaching device 25 of first robot 21 and possibly a coordinate system of x-ray source RQ and a coordinate system of patient table 8.

Furthermore, robot arms 23, 26, 32 of the three robots 21, 22, 31 were surveyed in advance, so that control device 27 of second robot 22 is also aware of information about the relative location of robot arms 23, 26 of first and second robots 21, 22, and control device 33 of third robot 31 is also aware of information about the relative location of robot arms 23, 32 of first and third robots 21, 31 with respect to each other. Information about the current position of robot arm 23 of first robot 21, movable by means of linear unit 4, is likewise conveyed by control device 24 of first robot 21 to control devices 27, 33 of second and third robots 22, 31 during the motion of attaching device 25 of first robot 21.

Hence it is possible for control device 27 of second robot 22 to calculate the current position and orientation of attaching device 25 of first robot 21 or of x-ray source RQ, in order, in turn, to activate the drives of second robot 22 by means of a computer program running on control device 27 of second robot 22, in such a way that attaching device 28 of second robot 22 and in particular a tool center point of x-ray receiver RQ is oriented so that the latter is at the predefined distance d from x-ray source RQ and is also aligned with the latter.

Control device 24 of first robot 21 conveys the information described above to control device 27 of second robot 22 continuously during the motion, so that control device 27 of second robot 22 is constantly able to activate the drives of second robot 22 so that x-ray receiver RE is constantly aligned with x-ray source RQ at distance d.

It is also possible for control device 33 of third robot 31 to calculate the current position and orientation of attaching device 25 of first robot 21 or of x-ray source RQ, in order in turn to activate the drives of third robot 31 by means of a computer program running on control device 33 of third robot 31 so that attaching device 34 of third robot 31, and in particular a tool center point of patient table 8, is oriented in such a way that it is always oriented relative to x-ray source RQ or to x-ray receiver RE constantly at a predefined and calculated distance from x-ray source RQ or from x-ray source RE.

The information described above is conveyed continuously by control device 24 of first robot 21 to control device 33 of third robot 31 during the motion, so that control device 33 of third robot 31 is always able to activate the drives of third robot 31 in such a way that, in particular according to one exemplary embodiment, patient table 8 is always in a constant orientation relative to x-ray source RQ or to x-ray receiver RE, so that living organism 3 is always positioned at half the distance d, i.e., centered between x-ray source RQ and x-ray receiver RE. It is also possible, however, that the distance between patient table 8 and x-ray receiver RE and the distance between patient table 8 and x-ray transmitter RS differ, but in particular always remain constant. The two distances may be for example at a ratio of 1:2, 2:3, 1:4.

In the case of the present exemplary embodiment, x-ray device 1 can be operated in a second operating mode. In the second operating mode, the physician for example moves x-ray source RQ manually, for example by guiding or pulling on first robot 21 or on x-ray source RQ. During the manual motion, control device 24 of first robot 21 continuously conveys information about the position and orientation of the coordinate system of attaching device 25 of first robot 21 and the position of first robot 21 with reference to linear unit 4.

On the basis of this information, the location of x-ray source RQ is always known to the control devices 27, 33 of the two other robots 22, 31 during the manual motion of first robot 21. Accordingly, control device 27 of second robot 22 is able to activate the drives of second robot 22 in such a way that the tool center point of x-ray receiver RE is always oriented relative to x-ray source RQ at distance d, so that x-ray source RQ and x-ray receiver RE are oriented relative to each other at distance d.

During the motion, control device 33 of third robot 31 is always able to activate the drives of third robot 31 so that patient table 8 is always oriented constantly relative to x-ray source RQ or to x-ray receiver RE, i.e. in particular centered between x-ray source RQ and x-ray receiver RE.

Figure 2:
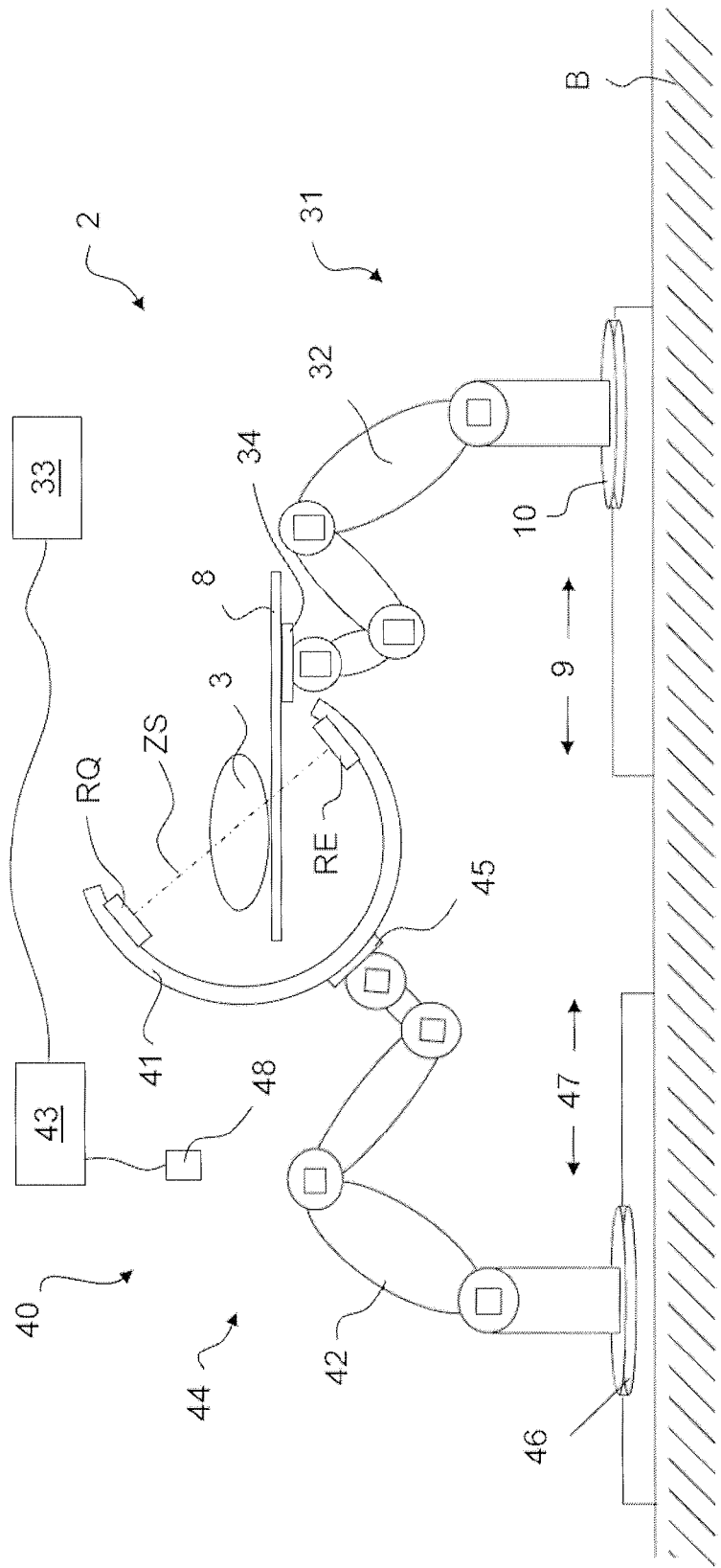

FIG. 2 shows another medical work station having another x-ray device 40 and adjustable patient support device 2 for supporting living organism 3. X-ray device 40 is another example of a medical technology apparatus, and in particular another example of an imaging medical technology apparatus.

The two medical work stations differ essentially in their x-ray devices 1, 40. The x-ray device 40 shown in FIG. 2 includes a carrier device 41 designed as a C-shaped arc, at the opposing ends of which x-ray receiver RE and x-ray source RQ are attached, so that the central beam ZS of the x-ray radiation produced by x-ray source RQ is able to strike x-ray receiver RE.

X-ray device 40 includes a fourth robot 44, which has a robot arm 42 and a control device 43. Robot arm 42 includes a plurality of members, joints connecting the members, drives connected to control device 43 in a manner not shown, in particular electric drives for moving the members, and an attaching device 45 for example in the form of a flange. A computer program runs on control device 43, so that control device 43 activates the drives in such a way that the position and orientation of attaching device 45 may be oriented essentially freely in space. The electric drives of fourth robot 44 each include, for example, an electric motor and possibly power electronics that activate the motors. Attached to attaching device 45 of robot arm 42 of fourth robot 44 is carrying device 41.

In the case of the present exemplary embodiment, fourth robot 44 or its robot arm 42 is attached to a liner unit 46, which is attached to the floor B of the medical work station and in particular is rail-bound, by means of which fourth robot 44 or its robot arm 42 is movable along a double arrow 47.

The linear unit 46 assigned to fourth robot 44 includes a drive, not depicted in the figures, to which control device 43 of fourth robot 44 is connected. During operation of fourth robot 44, control device 43 of fourth robot 44 controls the linear unit 46 assigned to fourth robot 44, in order to move robot arm 42 of fourth robot 44 along double arrow 47.

In the case of the present exemplary embodiment, it is provided that patient table 8 in one operating mode is always oriented constantly relative to x-ray source RQ or to x-ray receiver RE or to carrier device 41. This is realized as follows in the case of the present exemplary embodiment:

Control devices 33, 43 of third and fourth robots 31, 44 are designed as a master-slave system, control device 43 of fourth robot 44 being designed in the case of the present exemplary embodiment as the master, and control device 33 of third robot 31 being designed as the slave. On the basis of an input into a user interface 48 connected to control device 43, control device 43 controls the electric drives of fourth robot 44 and possibly linear unit 47 in such a way that attaching device 45 of fourth robot 44, and hence carrying device 41, execute a motion.

At the same time, control device 43 of fourth robot 44 conveys to control device 33 of third robot 31 information about the current position and orientation of its attaching device 45, which in the case of the present exemplary embodiment represents information about the position and orientation of a coordinate system assigned to this attaching device 45. Control device 33 of third robot 31 also has access to information about the relative location (orientation and position) between the coordinate system of attaching device 45 of third robot 44 and possibly a coordinate system of carrying device 41 and a coordinate system of patient table 8.

Furthermore, robot arms 32, 42 of third and fourth robots 31, 44 were surveyed in advance, so that information about the relative locations of robot arms 32, 42 of third and fourth robots 31, 44 relative to each other is also known to control device 33 of third robot 31. Information about the current position of robot arm 42 of first robot 44, movable by means of linear unit 46, is likewise conveyed by control device 43 of fourth robot 44 to control device 33 of third robot 31 during the motion of attaching device 45 of fourth robot 44.

Thus it is possible for control device 33 of third robot 31 to calculate the current position and orientation of attaching device 45 of fourth robot 44 or of carrying device 41, in order in turn to activate the drives of third robot 31 by means of a computer program running on control device 33 of third robot 31 so that attaching device 34 of third robot 31, and in particular a tool center point of patient table 8, is oriented in such a way that it is always oriented relative to carrying device 41 constantly at a predefined and calculated distance.

The information described above is conveyed continuously by control device 43 of fourth robot 44 to control device 33 of third robot 31 during the motion, so that control device 33 of third robot 31 is always able to activate the drive of third robot 31 in such a way that attaching device 34 of third robot 31, and in particular the tool center point of patient table 8, is oriented so that it is always in a constant orientation relative to carrying device 41.

In the case of the present exemplary embodiment, x-ray device 40 may be operated in a second operating mode, in which, for example, the physician moves carrying device 41 manually, in particular by pushing or pulling on robot arm 42 of fourth robot 44 or on carrying device 41. During the manual guiding, control device 43 of fourth robot 44 continuously conveys information about the position and orientation of the coordinate system of attaching device 45 of fourth robot 44, as well as possibly the position of fourth robot 44 with reference to linear unit 46.

On the basis of this information, the location of carrying device 41 is always known to control device 33 of third robot 31 during the manual motion of fourth robot 44. Accordingly, control device 33 of third robot 31 is always able to activate the drive of third robot 31 during the motion in such a way that patient table 8 is always oriented constantly relative to carrying device 41.

The invention claimed is:

1. A medical work station, comprising:
a medical technology apparatus comprising at least one first robot including a first robot arm with a plurality of links and a first attaching device, a first control device that controls motion of the first robot arm, and a medical technology device coupled to the first attaching device of the first robot arm; and
a patient support device comprising a second robot including a second robot arm with a plurality of links and a second attaching device, a second control device that controls motion of the second robot arm, and a patient table coupled to the second attaching device of the second robot arm;

wherein the first and second control devices are coupled with one another and are configured as a master-slave system with one of the first or second control devices configured as a master control device and the other of the first or second control devices configured as a slave control device;

wherein the master control device activates the slave control device such that in response to a first motion of the attaching device of the robot arm associated with the master control device, the slave control device moves its associated robot arm in such a way that the attaching device of the robot arm associated with the slave control device executes a second motion such that the relative orientation of the patient table and the medical technology device remains constant;

wherein the medical technology device comprises an x-ray source and an x-ray receiver; and wherein movement of the robot arm associated with the slave control device is such that the patient table remains positioned between the x-ray source and the x-ray receiver such that the distance between the patient table and the x-ray source, and the distance between the patient table and the x-ray receiver, can vary but are maintained at a predetermined ratio.

2. The medical work station according to claim 1, wherein the master control device automatically activates its associated robot arm such that its associated attaching device executes the first motion.

3. The medical work station according to claim 1, wherein the first motion is caused by manual guiding of at least a part of the medical technology device.

4. The medical work station according to claim 1, further comprising an input device operatively coupled to the master control device such that the master control device activates its associated robot arm to execute the first motion based on input received at the input device from a user.

5. The medical work station according to claim 1, wherein:
during the first motion the master control device conveys information about a current position and orientation of its associated attaching device to the slave control device; and
the slave control device moves its associated robot arm on the basis of the information from the master control device and on the basis of the current position and orientation of the attaching device of the robot arm associated with the slave control device such that the positions and orientations of the patient table and the medical technology device are always maintained constant relative to one another.

6. The medical work station according to claim 1, wherein the master control device is associated with the medical technology device and conveys information about a current position and orientation of the medical technology device to the slave control device.

7. The medical work station according to claim 1, wherein the master control device is associated with the patient table and conveys information about a current position and orientation of the patient table to the slave control device.

8. The medical work station according to claim 1, wherein the first motion is caused by manual guiding of the patient table.

* * * * *